United States Patent [19]

Kane et al.

[11] 3,932,539

[45] Jan. 13, 1976

[54] PROCESS FOR PREPARING UNSATURATED TERPENE ALCOHOLS

[75] Inventors: Bernard J. Kane, Atlantic Beach; Richard A. Von Genk, Jacksonville, both of Fla.

[73] Assignee: SCM Corporation, New York, N.Y.

[22] Filed: Feb. 14, 1972

[21] Appl. No.: 226,325

[52] U.S. Cl... 260/631.5; 260/247.7 K; 260/293.65; 260/293.9; 260/501.15; 260/567.6 M; 260/573; 260/577; 260/584 R
[51] Int. Cl.² .................. C07C 29/02; C07C 33/02
[58] Field of Search ................................. 260/631.5

[56] References Cited
UNITED STATES PATENTS
2,871,271  1/1959  Booth .......................... 260/631.5 X FOREIGN PATENTS OR APPLICATIONS
1,117,563  6/1962  Germany

OTHER PUBLICATIONS

D. Ginsburg, "Concerning Amines — Their Properties Preparation and Reactions," Permagon, (1967), pp. 73–83.

Mannich et al. "Berichte," 1936, pp. 2112–2115, 2121 and 2122.

*Primary Examiner*—R. Gallagher
*Assistant Examiner*—D. B. Springer
*Attorney, Agent, or Firm*—Richard H. Thomas

[57] ABSTRACT

An improved process for the preparation of unsaturated terpene alcohols such as myrcenol and cis and trans ocimenol is described. Acyclic terpene allylic halides are reacted with a tertiary amine of the formula hereinafter described to form the corresponding quaternary ammonium salt which is then acidified to remove the ethylenic unsaturation between the 6th and 7th carbon atom and adding a hydroxy substituent on the 7th carbon atom of the terpene halide salt. The hydrated terpene ammonium halide salt is made neutral and thermally decomposed into the unsaturated terpene alcohols. Myrcenol and ocimenol cis and trans are useful for their fragrance and aroma in perfumery and cosmetic manufacture.

10 Claims, No Drawings

PROCESS FOR PREPARING UNSATURATED TERPENE ALCOHOLS

This invention relates to an improved process for preparing valuable terpene alcohols from acyclic terpene allylic halides. More specifically this invention relates to an improved process for preparing unsaturated terpene alcohols such as:

A. Myrcenol (2-methyl-6-methylene-7-octene-2-ol).

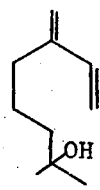

B. Cis-ocimenol (cis-2,6-dimethyl-5,7-octadiene-2-ol).

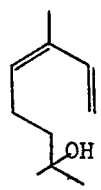

C. Trans-ocimenol (trans-2,6-dimethyl-5,7-octadiene-2-ol).

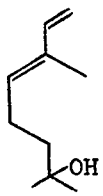

Terpene alcohols of the type produced by this invention are especially valuable because of their fragrance. Their odors are useful in citrus and floral fragrances employed in cosmetic and soap manufacture. Ocimenol, in particular, is especially prized in perfume compositions. Ocimenol is said to offer "new tonalities, freshness and rich cool notes, unobtainable with the natural citrus oil" in "Perfume and Flavor Chemicals" by S. Arctander (1969) no. 2389. Additionally, the esters of myrcenol and ocimenol are much prized for their odors.

Prior art processes for the manufacture of these terpene alcohols have suffered from many disadvantages. Processes for the production of myrcenol as described in U.S. Pat. Nos. 2,871,271 and in 2,947,780 give mixtures containing major quantities of other less desirable alcohols. Another process described in U.S. Pat. No. 3,075,003 produces none of the more desired alcohol, ocimenol. Moreover, this process requires highly specialized manufacturing equipment consisting of a low vacuum "wiping" still for the purification of intermediates. In yet another process, described in U.S. Pat. No. 3,549,679, it is necessary to use large quantities of a toxic and expensive compound, iron pentacarbonyl to produce myrcenol. Further, the process of that patent also gives none of the more valuable ocimenol. The process described in U.S. Pat. No. 3,344,171 requires the use of precious metals such as rhodium and iridium for the production of ocimenol. Moreover, the theory yield of ocimenol from myrcenol by this process is reported to be only 60%.

In summary, prior art processes for the manufacture of unsaturated terpene alcohols have encountered numerous problems and disadvantages such as (a) low yields, (b) impure mixtures of terpene alcohols containing major quantities of less desirable alcohols, (c) the need for expensive highly specialized process equipment, (d) high inefficiency, (e) require the use of expensive catalysts such as precious metals and/or toxic ingredients and (f) unstability of unsaturated terpene alcohols in that they tend to polymerize readily due to its conjugated double bond.

It is an object of this invention to provide an improved process for the production of unsaturated terpene alcohols such as myrcenol and cis and trans-ocimenol and mixtures thereof. It is a further object of this invention to provide a highly efficient commercially feasible process for the synthesis of unsaturated terpene alcohols such as myrcenol and cis and trans-ocimenol of high purity without the aforementioned problems of the prior art.

BRIEF DESCRIPTION OF THE INVENTION

Unsaturated terpene alcohols (conjugated dienic terpene alcohols) such as myrcenol and cis and trans-ocimenol are prepared by quaternizing an acyclic terpene allylic halide such as neryl, geranyl, and linalyl halides and mixtures thereof with a tertiary amine to form the corresponding quaternary ammonium salt. The tertiary amines useful for this invention are represented by the following formula:

wherein (a) $R_1$, $R_2$ and $R_3$ are lower alkyl groups having 1–2 carbon atoms, (b) $R_1$ and $R_2$ are joined as a heterocyclic residue and $R_3$ is a lower alkyl having 1–2 carbon atoms, (c) $R_1$ and $R_2$ are lower alkyl groups having 1–2 carbon atoms and $R_3$ is a cycloalkyl, aralkyl or aryl carbon compound.

After quaternization, the quaternary ammonium salt of the terpene allylic halide is acidified by adding an aqueous acid medium to the reaction mixture thereby removing the ethylenic un-saturation, between the 6th and 7th carbon of the terpene allylic halide salt and adding an hydroxy substituent on the 7th carbon of the terpene halide salt. Following hydration is neutralization of the hydroxy substituted terpene quaternary ammonium salt by base or aqueous alkaline solution and thereafter thermally decomposing the neutralized hydroxy substituted terpene quaternary salt to form the unsaturated terpene alcohols.

DETAILED DESCRIPTION OF THE INVENTION

In accordance with the invention, the first step of the process for preparing the unsaturated terpene alcohols such as myrcenol and ocimenol (cis and trans) is the quaternization step. An halo-substituted acyclic terpene is reacted with a tertiary amine of the formula heretofore described to form a quanternary ammonium salt of the terpene halide. Typical halo-substituted acyclic terpenes also referred to as acyclic terpene allylic halides which can be used for the quaternization reaction are linalyl halides, geranyl halides, and neryl halides. One common source of linalyl, geranyl, and neryl chlorides is the hydrochlorination of commercial myrcene using a copper catalyst to form crude myrcene hydrochloride described in U.S. Pat. No. 2,882,323. Myrcene hydrochloride contains about 60% neryl and geranyl chloride, 10% linalyl chloride, about 10–15% non-allylic terpene chlorides and the remainder is a mixture of terpene hydrocarbons. Myrcene hydrochloride is an intermediate produced in large volume for the synthesis of nerol, geraniol and citral. The following chemical reaction is illustrative of the quaternization step when neryl and geranyl chlorides are employed.

1–2 carbon atoms, (b) $R_1$ and $R_2$ are joined as a heterocyclic residue and $R_3$ is a lower alkyl having 1–2 carbon atoms, (c) $R_1$ and $R_2$ are lower alkyl groups having 1–2 carbon atoms and $R_3$ is a cycloalkyl, aralkyl or aryl carbon compound.

Tertiary amines useful for this reaction are those which generally give satisfactory rates of quaternization of alkyl halides. Typical of such amines represented by the formula heretofore described are aliphatic amines, such as trimethylamine, triethylamine and methyldiethylamine. Cyclic aliphatic amines such a N-methyl-piperidine and N-methyl morpholine are also effective. Examples of other effective amines are N-N-dimethylcyclohexylamine and N,N-dimethyl benzylamine. Sterically hindered tertiary amines, such as tri-n-butylamine, N-cyclohexyl morpholine, N-methyldicyclohexylamine and N-cyclohexyl piperidine as well

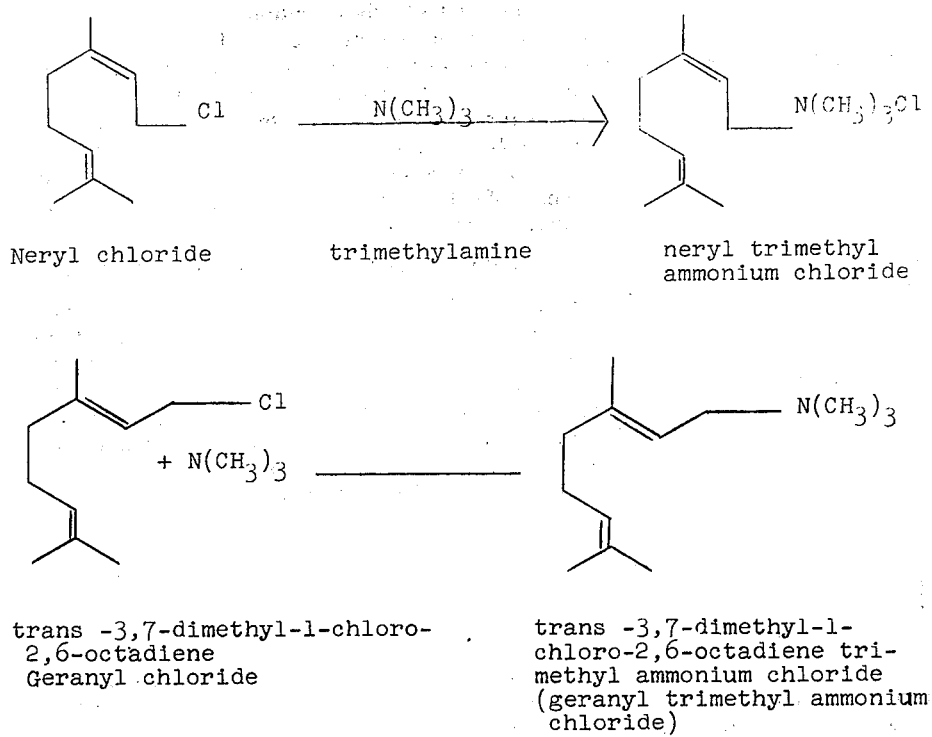

Neryl chloride     trimethylamine     neryl trimethyl ammonium chloride trans -3,7-dimethyl-1-chloro-2,6-octadiene
Geranyl chloride trans -3,7-dimethyl-1-chloro-2,6-octadiene trimethyl ammonium chloride
(geranyl trimethyl ammonium chloride)

Mixtures of acyclic terpene allylic halides are also reacted with the tertiary amine to form the quaternary ammonium salt of the terpene halide. Generally, the amount of tertiary amine reacted with the acyclic terpene allylic halide is not critical, usually an excess of the stoichiometric amount necessary for the quaternization reaction, from about 1.01 to about 2.00 moles per mole of the acyclic terpene allylic halides. The preferred ranges are 1.1 to 1.2 moles of the amine per mole of the terpene halide. Any excess tertiary amine used in the reaction can be readily recovered by known procedures.

Tertiary amines useful for the quaternization reactions are represented by the formula:

$$\begin{array}{c} R_1 \\ | \\ N-R_2 \\ | \\ R_3 \end{array}$$

wherein (a) $R_1$, $R_2$ and $R_3$ are lower alkyl groups having as tertiary-aromatic amines such as dimethylaniline, are useful, but only with long reaction times. Trimethylamine is the preferred tertiary amine for reasons of economy. Further, because trimethylamine has no hydrogens on a beta-carbon, the resultant quaternary ammonium hydroxide can eliminate in only one direction and thus give improved yields.

Quaternization temperature can range from −20°C to 100°C. Temperatures in the range of 20° to 60°C are preferred.

The quaternary ammonium salt of the terpene halide is a solid which precipitates as a product from the quaternization reaction. If the reaction mixture becomes too thick, solvents such as a mixture of menthadienes or aliphatic and aromatic hydrocarbons may be added to make the reaction mixture more fluid. Alternatively, water may be incrementally added. The amount of water is not critical. The amount would further depend on the nature of the quaternary ammonium salt. About 8% water based on the weight of myrcene hydrochloride is sufficient to form an aqueous solution of the trimethyl quaternary ammonium chloride. Additional quantities can be used but are not preferred because large quantities would promote the hydrolysis of terpene allylic halides to the corresponding alcohols. Quaternization reaction time is complete when all the allylic terpene halides are absent from the reaction mixture. The progress of the reaction can be monitored by removing samples from the oil phase and determining the concentration of the allylic halides by vapor phase chromatography or infra-red analysis.

STEP II — HYDRATION REACTION

Following quaternization is hydration of the quaternary ammonium salt of the terpene halide with an aqueous acid to form a hydroxy substituent on the seventh carbon atom. The quaternary ammonium salts from the quaternization step are solid compounds and were found to be highly water soluble. This high water solubility has two valuable features. One, the water solubility facilitates a more rapid hydration of the 6,7-double bond. Secondly, the quaternary ammonium salts can be purified easily from the unreacted chloride compounds and hydrocarbons, originally present in the crude myrcene hydrochloride which are not water soluble. The following reaction is illustrative of the hydration step:

One normal acid will give complete hydration in 24 hours at 25°C. If 3.4 N acid is used, hydration is complete in 4 hours.

The progress of the hydration step may be followed by removing a sample from the reaction and subjecting it to heat in the presence of aqueous alkali. The volatile oil formed is then analyzed by vapor phase chromatography to determine the degree of hydration of the 6,7-double bond.

STEP III — NEUTRALIZATION

Following the hydration step the aqueous layer is neutralized with solid base or an aqueous alkaline solution (See Chart I). Performance of this step is not critical but for best yields it is preferred that the aqueous solution of the hydrated quaternary ammonium compounds be neutralized before subjecting this solution to the conditions of the next step. In the decomposition the temperature is elevated and if the acidic aqueous solution is momentarily heated to an elevated temperature, there results some dehydration of the 7-hydroxy substituent on the allylic terpene quaternary ammonium compound. The terpene alcohols can be made without the neutralization step but neutralization is preferred for economy, efficiency and higher yields.

The base may be added as a solid or as an aqueous solution. The concentration of the base may be 100%–5%. Preferably a sodium hydroxide solution

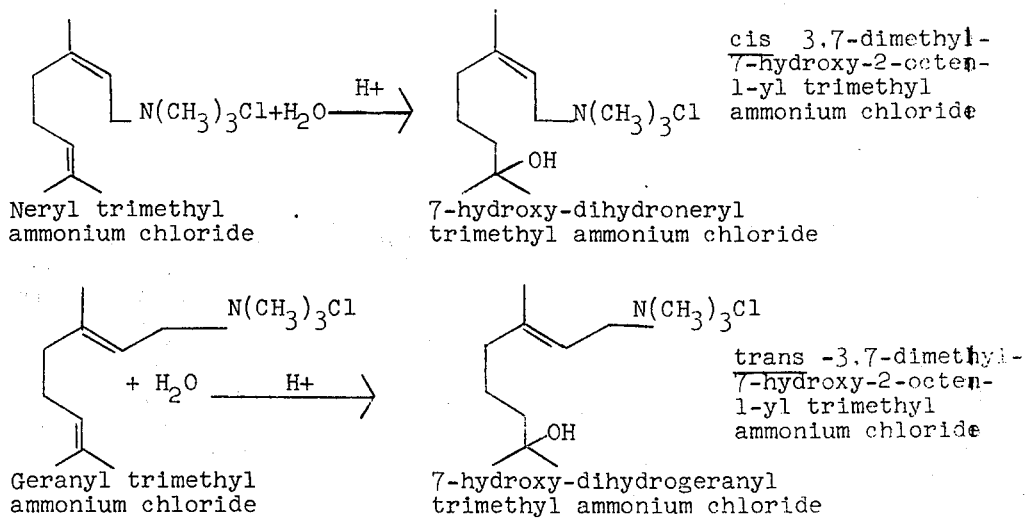

Neryl trimethyl ammonium chloride 7-hydroxy-dihydroneryl trimethyl ammonium chloride cis 3,7-dimethyl-7-hydroxy-2-octen-1-yl trimethyl ammonium chloride Geranyl trimethyl ammonium chloride 7-hydroxy-dihydrogeranyl trimethyl ammonium chloride trans -3,7-dimethyl-7-hydroxy-2-octen-1-yl trimethyl ammonium chloride The hydration reaction is started after the termination of the quaternization reaction by the addition of water and acid to catalyze hydration. Acids useful for the hydration are mineral acids such as HCl, $H_2SO_4$, and $H_3PO_4$.

The normality of the acid used for hydration ranges from 1.0 N to 6.0 N. Preferred acid normality is 1.2 N to 3.0 N. The amount of water added is not critical. For economy and efficiency water is added first to dissolve the quaternary ammonium terpene halide salt in an aqueous solution and to separate any hydrocarbons and terpene non-allylic halides in a separate oil layer.

The aqueous layer is then washed with a suitable paraffinic or aromatic hydrocarbon solvent to remove the last traces of any unreacted terpene compounds. Generally the temperature of hydration ranges from 15° to 60°C. Preferred temperature is room temperature. Time of the hydration reaction is dependent upon normality of the acid used.

having a concentration between 10% and 30% is employed for efficiency and economy. Similar results were obtained with other concentrations and with other bases such as potassium hydroxide or sodium carbonate. The neutralization can be carried out at temperatures between −15° and 60°C. Preferably the hydroxy substituted terpene quaternary ammonium salt solution is cooled to about room temperature, 25°C, during neutralization.

During neutralization the quaternary ammonium hydroxide of the hydroxy substituted terpene is formed. However, it is postulated that it may not be exclusively in the hydroxide form. The reaction mixture may contain terpene quaternary ammonium hydroxide in the form of a solution of ions.

STEP IV — THERMAL DECOMPOSITION

The final step of the process is the thermal decomposition of the quaternary ammonium hydroxide of the hydroxy substituted terpene. (See Chart I). Thermal decomposition was accomplished at a temperature range of above about 100°C to below about 170°C. The preferred temperature of decomposition is 125°C to 140°C. The rate of decomposition was found to be slow below 110°C.

The quaternary ammonium hydroxide is decomposed

As the quaternary ammonium hydroxide decomposes, the unsaturated terpene alcohol products formed are readily separated by conventional phase separation methods such as steam distillation, decantation, cohobation; unsaturated terpene alcohols are advantageously removed from the alkaline solution rapidly to prevent polymerization.

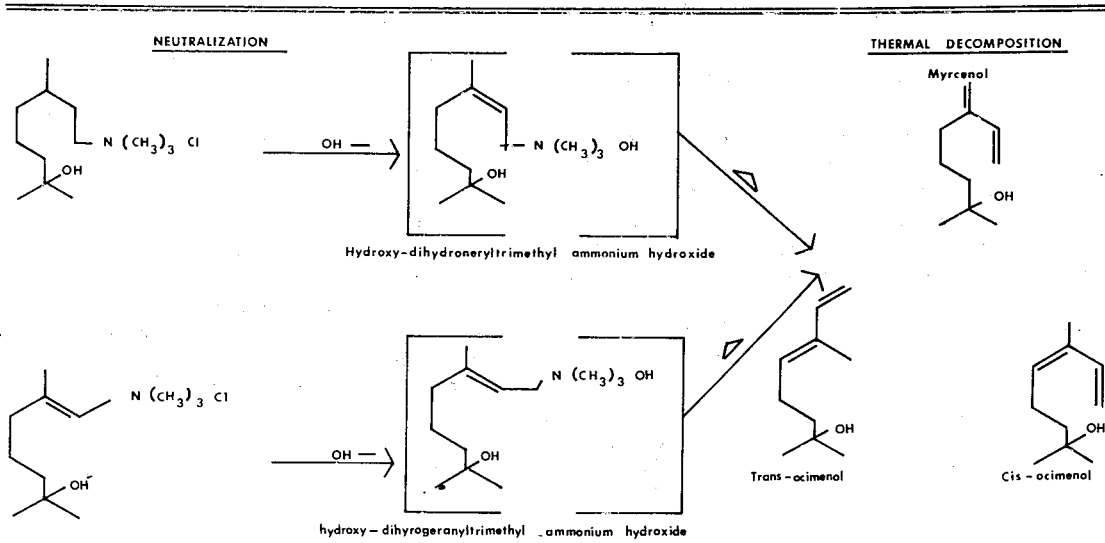

CHART I for convenience preferably in the presence of sodium hydroxide solution. Alternately, the quaternary ammonium hydroxide can be heated alone in order to bring about decomposition. This latter alternative is commercially less attractive because of the difficulty of isolating the quaternary ammonium hydroxide.

In the preferred manner of operation, the neutralized aqueous solution of the quaternary ammonium salt is fed to a refluxing solution of a base, such as sodium hydroxide or potassium hydroxide, at a rate proportional to the rate of steam distillation of the myrcenol and ocimenol from the decomposition.

In order to achieve more rapid rates of decomposition, the reaction temperature must be in the vicinity of at least 120°C. To achieve such a temperature, the sodium hydroxide solution must be at least 25% in concentration. Weaker concentrations tend to give lower reflux temperatures and thus slower rates. Good results are obtained using solutions containing 50–60% aqueous alkali which give reflux temperatures of 135° to 140°C. The preferred range is 125° to 140°C. Concentration of 10–70% can be used.

The ratio of myrcenol to cis and trans-ocimenol was found to be dependent upon the concentration of the alkaline solution employed during the thermal decomposition. The amount of myrcenol increased with decreasing concentration of alkali. For example, when an alkaline solution was employed having a concentration of 50–60% during the thermal decomposition reaction the product ratio was 60% myrcenol and 40% cis and trans-ocimenol. When an alkaline solution having a concentration of 25% was employed, the ratio was 80% myrcenol and 20% cis and trans-ocimenol.

The rate of decomposition is dependent primarily upon the temperature of decomposition. When the temperature of the reaction is less than 110°C, decomposition is slow. Optionally, the rate of decomposition can be increased by the addition of high boiling solvent such as ethylene glycol, or by the addition of neutral salts such as NaCl, Na acetate, sodium formate and sodium phosphate.

The following examples show ways in which the invention has been practiced but should not be construed as limiting the invention. All parts are parts by weight and all temperatures are degrees Centigrade unless otherwise indicated.

EXAMPLE 1

The starting material, prepared by hydrochlorination of commercial myrcene using a copper catalyst, contained about 10% linalyl chloride and 60% neryl and geranyl chlorides, about 10–15% non-allylic terpene chlorides and the remainder was a mixture of various terpene hydrocarbons.

Trimethylamine (285 grams) was added gradually over 4 hours at 20°–30°C to 1000 grams myrcene hydrochloride. In order to make the reaction more fluid, 500 grams of a mixture of terpene hydrocarbons is added to the reaction at the beginning. The reaction mixture containing solid quaternary ammonium chlorides was stirred for an additional 16 hours at 20°–30°C. Then 1000 grams of water was added to dissolve the solid.

The oil layer containing terpene hydrocarbons and unreactive terpene chlorides after separation weighed 766 grams. The water layer was washed once with 200 grams of heptane to remove occluded oils. The water layer, which weighed 2019 grams, was diluted with 1615 grams of water and acidified with 385 grams 37% aqueous hydrochloric acid. The mixture was allowed to stand for 24 hours. The normality of the acid layer was 1.3N.

The solution was then carefully made alkaline at 25°C with cooling by the addition of an aqueous solution containing 324 grams of sodium hydroxide. The hydrated geranyl trimethyl ammonium hydroxide remained dissolved in the water layer.

The aqueous solution was then added gradually to a refluxing solution of 1800 grams sodium hydroxide in 2700 grams of water. The rate was such that the volatile alcohols, formed on decomposition, could be readily removed by steam distillation. The decomposition temperature was maintained at 120°–130°C.

A total of 669 grams of steam distilled alcohols was obtained. Vapor phase chromatographic analysis showed the myrcenol content to be 80% and the cis- and trans-ocimenols to be 20%.

EXAMPLE 2

Trimethylamine (340 grams) was added to 1000 grams of myrcene hydrochloride under the same conditions as in Example 1. The reaction was then diluted with 1000 grams of water. The unreacted oils, including the 500 grams of terpene hydrocarbons which were added during the trimethylamine addition, were not separated from the oil layer.

To the reaction was then added 600 grams 37% hydrochloric acid solution. The normality of the water layer was 2.6N. Analysis of the water layer after 6 hours indicated that the hydration was complete.

The water layer was then separated from the oil layer which weighed 757 grams. The water layer after washing with 200 grams heptane was carefully made alkaline (pH greater than 9) using cooling at 25°C. with the addition of 290 grams NaOH (97%).

The water layer, now weighing 2973 grams, was added gradually to a refluxing solution of 300 grams NaOH, 615 grams sodium acetate and 900 grams of water. The temperature of the decomposition was maintained between 125°–130°C. At completion the steam distilled oil weighed 540 grams and analyzed 79.4% myrcenol and 18.6% cis- and trans-ocimenols.

The alcohol product may then be given a distillation at reduced pressure to produce perfume quality myrcenol and ocimenols. An oxidation inhibitor such as 2,6-dibutyl-p-cresol can be added to the distillation to give better yields.

The alcohol product also may be reacted with acetic anhydride at room temperature with a few precent mineral acid catalyst. After a suitable reaction period, the reaction is washed up and the mixed acetates are distilled to give a perfume grade mixture of myrcenyl and cis- and trans-ocimenyl acetates.

EXAMPLE 3

Trimethylamine (285 grams) was added to 1000 grams of myrcene hydrochloride over 4 hours at 20°–30°C. The reaction was made more fluid by the addition of 500 grams of mixed terpene hydrocarbons. After 16 hours, 1000 grams of water was added with mixture. The separated oil layer weighed 766 grams and the water layer after washing with 200 grams heptane weighed 2019 grams. The water layer was then diluted with 2000 grams water and acidified with 393 grams of 37% hydrochloric acid. After 24 hours at room temperature, the hydration was virtually complete.

Then the water layer was made very strongly alkaline (pH 14) by the gradual addition of 1023 grams of sodium hydroxide. The hydrated quaternary ammonium compounds separated as a thick, oil layer. This oil layer, after separation, weighed 1958 grams.

The oil layer was then fed gradually to a refluxing solution of 900 grams sodium hydroxide, 1845 grams sodium acetate and 2700 grams water. The oil distillate weighed 573 grams and contained 79.2% myrcenol and 20.8% cis- and trans-ocimenols. Much of the aqueous distillate was returned to the decomposition vessel so as to maintain a reaction temperature of 125°–130°C.

EXAMPLE 4

The conditions of Example 3 were repeated except that the hydroxygeranyltrimethylammonium hydroxide oil layer was decomposed to alcohols by gradually adding it to a refluxing solution of 300 grams sodium hydroxide and 2982 grams ethylene glycol. The temperature of the decomposition was maintained at 165°–170°C. throughout the run. The crude product weighed 591 grams and contained 81.9% myrcenol and 17.3% ocimenols.

EXAMPLE 5

Trimethylamine (294 grams) was added gradually to a mixture of 1000 grams of myrcene hydrochloride and 80 grams of water at 20°–30°C. over 4 hours. The reaction was then stirred for an additional 16 hours at about 25°C. The reaction mixture remained fluid throughout.

To the mixture was added 1160 grams of water. The aqueous layer after separation weighed 1914 grams and the oil layer weighed 304 grams. VPC analysis of the oil layer showed no unreacted terpene allylic chlorides and only traces of alcohols.

The aqueous layer was washed with 100 grams of heptane to remove occluded oils and then acidified with 225 grams of 37% hydrochloric acid solution. The hydration was virtually complete after 24 hours at room temperature.

The solution was neutralized by the gradual addition of 215 grams of sodium hydroxide with agitation and cooling. The neutralized solution was then fed gradually to a refluxing solution of 1040 grams NaOH in 975 grams of water. A total of 526 grams of alcohol mixture was obtained which by VPC analysis contained 3.1% hydrocarbons, 63.5% myrcenol and 33.4% ocimenols.

We claim:

1. An improved process for preparing a mixture of terpene alcohols consisting essentially of myrcenol, and at least 20% cis-ocimenol and trans-ocimenol, comprising the steps of:

A. reacting an acyclic terpene allylic halide selected from the group consisting of geranyl, neryl and linalyl halides and mixtures thereof with a tertiary amine at a temperature in the range of about −20°C to about 100°C to form a corresponding quaternary ammonium halide salt, said tertiary amine being a compound represented by the formula:

wherein
a. $R_1$, $R_2$ and $R_3$ are lower alkyl groups having 1–2 carbon atoms,
b. $R_1$ and $R_2$ are lower alkyl groups having 1–2 carbon atoms and $R_3$ is a 6 or 7 carbon cycloalkyl, aralkyl or aryl hydrocarbon group:
c. or said tertiary amine is a compound selected from the group consisting of N-alkyl morpholine, N-alkyl piperidine, the alkyl group being ethyl or methyl, N-cyclohexyl morpholine, N-cyclohexyl piperidine and N-methyl dicyclohexylamine and tri-n-butylamine;

B. acidifying said salt by adding to said reaction mixture a 1.0 N to 6.0 N aqueous solution of a mineral acid of the group consisting of sulfuric acid, hydrochloric acid, and orthophosphoric acid to hydrate the 6-7 ethylenic unsaturation of said quaternary ammonium salt to form an hydroxy substituent on the seventh carbon atom;

C. neutralizing said hydroxy substituted terpene quaternary ammonium halide salt by adding to said mixture an aqueous solution of carbonate or hydroxide alkaline base to form the corresponding quaternary ammonium hydroxide; and D. thereafter thermally decomposing in the presence of an alkaline solution having a concentration of at least 25% at a temperature above about 100°C to below about 170°C the 7-hydroxy substituted terpene quaternary ammonium hydroxide to form a mixture the major portion of which consists essentially of myrcenol, cis-ocimenol and trans-ocimenol.

2. The process of claim 1 wherein the tertiary amine is trimethylamine.

3. The process of claim 1 wherein the normality of acid used for acidifying step (B) is 1.0 N to 6.0 N.

4. The process of claim 1 wherein the concentration of the alkali used for the neutralization step is 100% to 5%.

5. The process of claim 1 wherein the neutralization step is done at a temperature of −15° to 60°C, the temperature range for thermal decomposition being 125° to 140°C.

6. The process of claim 1 wherein the acyclic terpene allylic halide for the quaternization step is selected from the group consisting of geranyl chloride, neryl chloride and linalyl chloride.

7. The process of claim 1 wherein the tertiary amine is reacted with the acyclic terpene allylic halide at a temperature of 20° to 60°C.

8. The process of claim 1 wherein said aqueous solution of step (C) is a carbonate or hydroxide of sodium or potassium.

9. An improved process for preparing a mixture of terpene alcohols consisting essentially of myrcenol, and at least 20% cis-ocimenol and trans-ocimenol, comprising the steps of:

A. reacting an acyclic terpene allylic halide selected from the group consisting of geranyl, neryl and linalyl halides and mixtures thereof with a tertiary amine at a temperature in the range of about −20°C to about 100°C to form a corresponding quaternary ammonium halide salt, said tertiary amine being a compound represented by the formula:

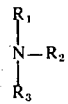

wherein
  a. $R_1$, $R_2$ and $R_3$ are lower alkyl groups having 1-2 carbon atoms,
  b. $R_1$ and $R_2$ are lower alkyl groups having 1-2 carbon atoms and $R_3$ is a 6 or 7 carbon cycloalkyl, aralkyl or aryl hydrocarbon group;
  c. or said tertiary amine is a compound selected from the group consisting of N-alkyl morpholine, N-alkyl piperidine, the alkyl group being ethyl or methyl, N-cyclohexyl morpholine, N-cyclohexyl piperidine and N-methyl dicyclohexylamine and tri-n-butylamine B. acidifying said salt by adding to said reaction mixture a 1.0 N to 6.0 N aqueous solution of a mineral acid of the group consisting of sulfuric acid, hydrochloric acid, and orthophosphoric acid to hydrate the 6-7 ethylenic unsaturation of said quaternary ammonium salt to form an hydroxy substituent on the seventh carbon atom;

C. thereafter thermally decomposing in the presence of an alkaline solution having a concentration of at least 25% at a temperature above about 100°C to below about 170°C the hydrated quaternary ammonium compound to form a mixture the major portion of which consists essentially of myrcenol, cis-ocimenol and trans-ocimenol.

10. The process of claim 9 wherein the temperature range for the thermal decomposition is 125° to 140°C.

* * * * *